US009283332B2

(12) United States Patent
Unverdorben

(10) Patent No.: US 9,283,332 B2
(45) Date of Patent: Mar. 15, 2016

(54) INTELLIGENT AIR BUBBLE DETECTOR AND COUNTERS FOR AUTOMATED INFUSION SYSTEMS

(75) Inventor: Martin Unverdorben, Pottstown, PA (US)

(73) Assignee: B. Braun Medical, Inc., Bethlehem, PA (US)

( * ) Notice: Subject to any disclaimer, the term of this patent is extended or adjusted under 35 U.S.C. 154(b) by 483 days.

(21) Appl. No.: 13/408,219

(22) Filed: Feb. 29, 2012

(65) Prior Publication Data

US 2013/0226130 A1 Aug. 29, 2013

(51) Int. Cl.
*A61M 1/00* (2006.01)
*A61M 5/36* (2006.01)

(52) U.S. Cl.
CPC ..................... *A61M 5/365* (2013.01)

(58) Field of Classification Search
CPC ..................................... A61M 5/365
USPC ................. 604/151, 65–67; 417/282
See application file for complete search history.

(56) References Cited

U.S. PATENT DOCUMENTS

| | | | |
|---|---|---|---|
| 4,114,144 A | 9/1978 | Hyman | |
| 4,366,384 A | 12/1982 | Jensen | |
| 4,367,736 A | 1/1983 | Gupton | |
| 5,260,665 A | 11/1993 | Goldberg et al. | |
| 5,382,232 A | 1/1995 | Hague et al. | |
| 5,394,732 A * | 3/1995 | Johnson et al. | 73/19.1 |
| 5,536,471 A | 7/1996 | Clark et al. | |
| 6,408,679 B1 | 6/2002 | Kline-Schoder et al. | |
| 6,488,660 B1 * | 12/2002 | Futterknecht | 604/129 |
| 6,616,633 B1 | 9/2003 | Butterfield et al. | |
| 7,141,037 B2 | 11/2006 | Butterfield et al. | |
| 7,338,470 B2 * | 3/2008 | Katz et al. | 604/122 |
| 7,981,082 B2 | 7/2011 | Wang et al. | |
| 8,622,979 B2 | 1/2014 | Hungerford et al. | |

FOREIGN PATENT DOCUMENTS

| | | |
|---|---|---|
| FR | 2361644 A1 | 3/1978 |
| WO | WO 81/00519 | 3/1981 |
| WO | WO 2009/026420 A1 | 2/2009 |

OTHER PUBLICATIONS

International Search Report dated May 7, 2013, application No. PCT/US2013/027877.
Written Opinion of the International Searching Authority, corresponding to application No. PCT/US2013/027931, dated Sep. 2, 2014.
Written Opinion of the International Searching Authority, corresponding to application No. PCT/US2013/027877, dated Sep. 2, 2014.

* cited by examiner

*Primary Examiner* — Rebecca E Eisenberg
(74) *Attorney, Agent, or Firm* — RatnerPrestia

(57) ABSTRACT

Systems and methods for sensing bubbles during fluid infusion are disclosed. An infusion device comprises a pathway, a pump adjacent the pathway, one or more bubble sensors, and first and second modules. The pump alters the pathway to pump fluid through tubing received in the pathway. The bubble sensors are configured to detect bubbles in the fluid being pumped through the tubing. The first module is configured to generate a first alarm condition when the bubble sensors detect a bubble having a first volume above a first preselected threshold. The second module is configured to generate a second alarm condition when the bubble sensors detect a plurality of bubbles over a preselected period of time having a combined volume above a second preselected threshold. A third module may be also be used to record a total combined volume of bubbles detected by the bubble sensors during an infusion event.

13 Claims, 2 Drawing Sheets

INTELLIGENT AIR BUBBLE DETECTOR AND COUNTERS FOR AUTOMATED INFUSION SYSTEMS

FIELD OF THE INVENTION

The present invention relates generally to infusion systems and, more particularly, to systems and methods for sensing bubbles during fluid infusion.

BACKGROUND OF THE INVENTION

During medical treatment, it is often necessary to infuse fluids, such as medication or nutrients, into a patient's circulatory system. Conventionally, infusions are performed using infusion devices, which may include one or more pumps to infuse fluid to the patient at a predetermined rate and time. These infusion devices may be programmed according to predetermined infusion protocols, which are based, for example, on the fluid to be infused or the particular patient.

For safety purposes in a medical treatment setting, it is necessary to identify air bubbles that form in the fluid or from the outside and penetrate into the fluid being infused. Accordingly, conventional infusion devices include sensors configured to generate an alarm when air bubbles are detected. However, these conventional sensors may be improperly triggered by "micro-bubbles" (which are not harmful to the patient) that cling to the inside of the infusion tubing. Accordingly, improved systems and methods for sensing bubbles during fluid infusion are desired.

SUMMARY OF THE INVENTION

Aspects of the present invention relate to systems and methods for sensing bubbles during fluid infusion.

In accordance with one aspect of the present invention, an infusion device is disclosed. The infusion device comprises a pathway, at least one pump adjacent the pathway, one or more bubble sensors positioned adjacent the pathway, and first and second modules. A single bubble sensor with split vision is also envisioned. The pathway is adapted to receive tubing. The at least one pump alters the pathway to pump fluid through the tubing when the tubing is received in the pathway. The one or more bubble sensors are configured to detect bubbles in the fluid being pumped through the tubing. The first module is in communication with the one or more bubble sensors. The first module is configured to generate a first alarm condition when the one or more bubble sensors detect a bubble having a first volume above a first preselected threshold. The second module is in communication with the one or more bubble sensors. The second module is configured to generate a second alarm condition when the one or more bubble sensors detect a plurality of bubbles over a preselected period of time having a combined volume above a second preselected threshold.

The infusion device may further include a third module. The third module is in communication with the one or more bubble sensors. The third module is configured to record a total combined volume of bubbles detected by the one or more bubble sensors over a preselected period of time, typically the time of one or several infusions. It is envisioned that more than three modules could be used, with the additional modules being used to perform various additional calculations.

In accordance with another aspect of the present invention, a method for sensing bubbles during fluid infusion is disclosed. The method comprises pumping fluid through tubing with at least one pump of an infusion device, detecting bubbles in the fluid being pumped through the tubing with one or more bubble sensors, generating a first alarm condition when the one or more bubble sensors detect a bubble having a first volume above a first preselected threshold, and generating a second alarm condition when the one or more bubble sensors detect a plurality of bubbles over a preselected period of time having a combined volume above a second preselected threshold.

BRIEF DESCRIPTION OF THE DRAWINGS

The invention is best understood from the following detailed description when read in connection with the accompanying drawings, with like elements having the same reference numerals. When a plurality of similar elements are present, a single reference numeral may be assigned to the plurality of similar elements with a small letter designation referring to specific elements. When referring to the elements collectively or to a non-specific one or more of the elements, the small letter designation may be dropped. This emphasizes that according to common practice, the various features of the drawings are not drawn to scale unless otherwise indicated. To the contrary, the dimensions of the various features may be expanded or reduced for clarity. Included in the drawings are the following figures.

DETAILED DESCRIPTION OF THE INVENTION

The exemplary systems and methods disclosed herein are directed toward infusing a fluid to a patient. The disclosed embodiments are usable in systems where it is necessary or desirable to accurately detect the formation of bubbles in the fluid being infused. In particular, the disclosed embodiments may be particularly suitable for use in tracking the total volume of air bubbles formed in the fluid being infused.

Generally, the embodiments described herein include one or more bubble sensors positioned adjacent a fluid pathway of an infusion device. The infusion device includes one module (herein referred to as the first module, without claiming any sequence) coupled to the bubble sensors to detect any bubble having a volume exceeding a preselected threshold. The infusion device includes another module (herein referred to as the second module, without claiming any sequence) coupled to the bubble sensors to detect bubbles having a combined volume exceeding a preselected volume threshold within a preselected period of time. The infusion device may trigger an alarm whenever any of these thresholds are exceeded. The infusion device also includes yet another module (herein referred to as the third module, without claiming any sequence) coupled to the bubble sensors to record a total combined volume of bubbles detected by the one or more bubble sensors over a preselected period of time. This module may also trigger an alarm when a preselected combined volume is exceeded, or may not generate any alarm, and merely display the accumulated volume. Additional modules may be added.

Figure 1:
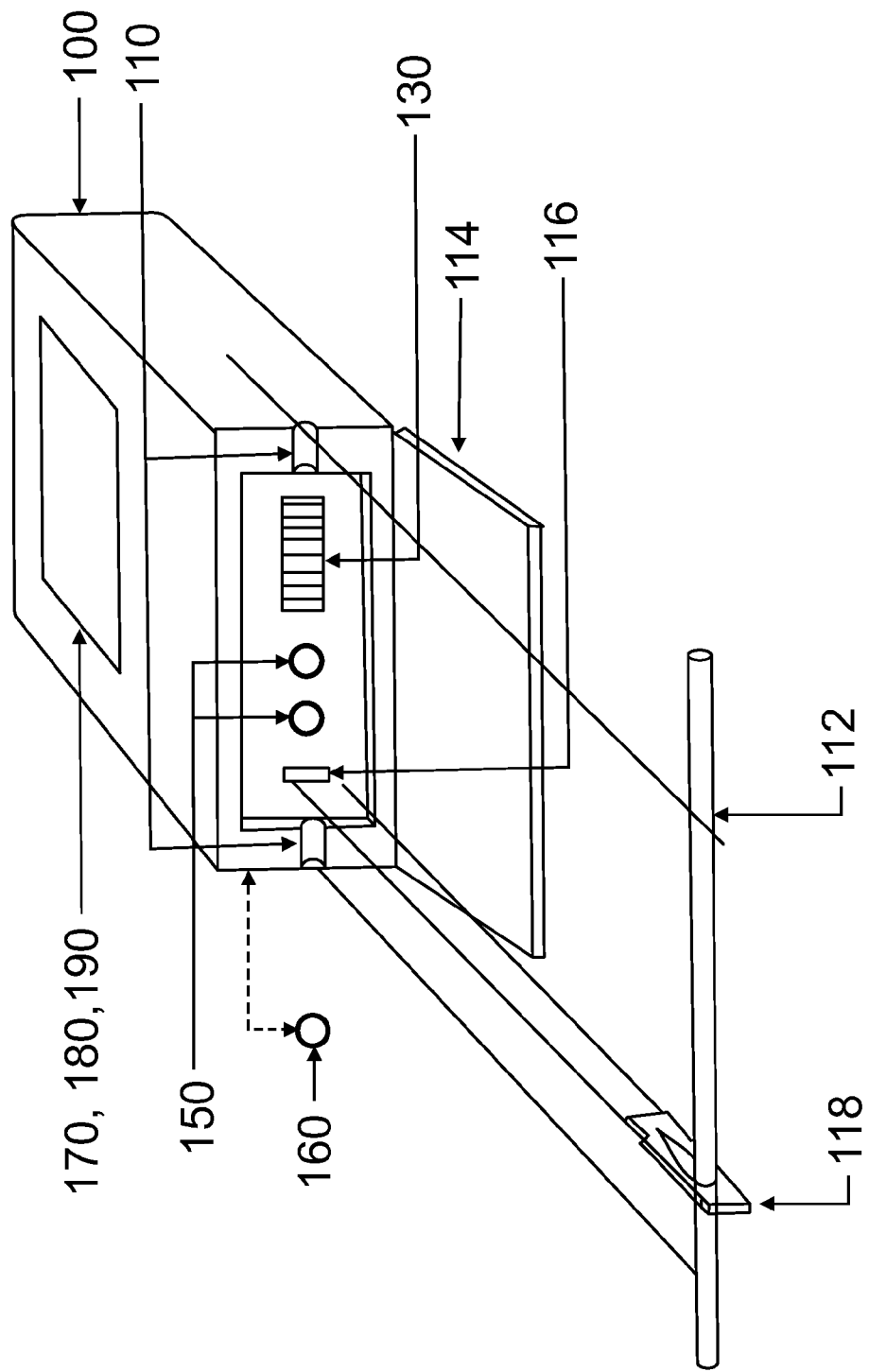
FIG. 1 is a diagram illustrating an exemplary infusion device in accordance with aspects of the present invention.

Referring now to the drawings, FIG. 1 illustrates an exemplary infusion device 100 in accordance with aspects of the present invention. Infusion device 100 is configured to infuse fluid (e.g. medication) to a patient. As a general overview, infusion device 100 includes a pathway 110, a pump 130, one or more bubble sensors 150, a first module 170, and a second module 180. At least one remote bubble sensor is also envisioned. Additional details of infusion device 100 are described herein.

Pathway 110 is adapted to receive a pump set. The pump set includes tubing 112 configured to receive fluid from a fluid container (not shown). As used herein, the term "pathway" refers to any structure (such as a slot, retainer, or groove) adapted to receive and/or retain tubing 112 of the pump set. Pathway 110 may include a guide adapted to secure tubing 112 of the pump set in a desired location and orientation within infusion device 100. In an exemplary embodiment, infusion device 100 includes a door 114 adapted to secure pump set tubing 112 within pathway 110 when closed, as shown in FIG. 1. Infusion device 100 may also include a recess 116 adapted to receive an attachment 118 (such as a clamp) of the pump set. Recess 116 may be usable to properly key the pump set tubing 112 within pathway 110 (i.e. ensure that the pump set is facing a proper direction).

Pump 130 is positioned adjacent pathway 110. Pump 130 is adapted to alter pathway 110 in order to pump fluid through pump set tubing 112 when the tubing 112 is received in pathway 110. In an exemplary embodiment, pump 130 is a peristaltic pump. Suitable pumps for use as an infusion pump 130 will be known to one of ordinary skill in the art from the description herein.

Bubble sensors 150 are positioned adjacent pathway 110 of infusion device 100. Bubble sensors 150 are configured to detect bubbles in the fluid being pumped through the tubing 112 by pump 130. As shown in FIG. 1, where multiple bubble sensors are used, one bubble sensor 150 may be positioned downstream from another bubble sensor 150. This may be desirable in order to increase the accuracy of bubble detection of infusion device 100. Additionally, in an exemplary embodiment, a remote bubble sensor 160 may be provided. Remote bubble sensor 160 may be removably connected to infusion device 100. Suitable bubble sensors for use as bubble sensors 150 and 160 will be known to one of ordinary skill in the art from the description herein.

Infusion device 100 includes at least one processor that controls the operation of infusion device 100. For example, the processor controls the programming of infusion device 100 with at least one infusion protocol, and coordinates the operation of pump 130 in accordance with the at least one infusion protocol. As is explained in greater detail below, the processor also monitors data from bubble sensors 150 to determine whether there are bubbles in the fluid being pumped by pump 130.

The at least one processor includes a number of modules that process data from bubble sensors 150, and that may be configured to generate alarms based on the output of bubble sensors 150. Each module may be implemented by its own distinct processor or group of processors, or a single processor may be used to implement multiple modules. Exemplary embodiments of the modules are described herein. Suitable processors for implementing the modules will be understood by one of skill in the art from the description herein.

First module 170 is a single bubble counter module. First module 170 is in communication with bubble sensors 150, and is configured to generate a first alarm condition when the bubble sensors 150 detect a single bubble having a first volume above a first preselected threshold. In an exemplary embodiment, a user of infusion device 100 may preselect a threshold volume for the first module 170. The threshold may be within the range of 0.02-0.30 ml. First module 170 may then monitor data from bubble sensors 150 until a bubble sensor 150 detects a single bubble having a volume exceeding the preselected threshold. When this happens, first module 170 generates an "air bubble" alarm condition. The air bubble alarm condition indicates that a single air bubble having the preselected volume has been identified. First module 170 may be programmed to display an air bubble alarm on a display device of infusion device 100. First module 170 may also be programmed to deactivate pump 130 until the detected bubble is cleared from tubing 112.

Second module 180 is an accumulated volume counter module. Second module 180 is in communication with bubble sensors 150, and is configured to generate a second alarm condition when the bubble sensors 150 detect a plurality of bubbles over a preselected period of time having a combined volume above a second preselected threshold. In an exemplary embodiment, a user of infusion device 100 may preselect a period of time and a threshold volume for the second module 180. The period of time may be within the range of 1-15 minutes, and the volume threshold may be within the range of 0.5-3.8 ml. Second module 180 may then monitor data from bubble sensors 150 until the bubble sensors 150 have detected a plurality of bubbles that collectively have a volume exceeding the preselected threshold within the preselected period of time. When this happens, second module 180 generates an "accumulated air volume" alarm condition. The accumulated air volume alarm condition indicates that a plurality of air bubbles having the combined preselected volume have been identified. Second module 180 may be programmed to display an accumulated air volume alarm on a display device of infusion device 100. Second module 180 may also be programmed to deactivate pump 130 until at least a portion of the detected bubbles are cleared from tubing 112.

It will be understood from the description herein that infusion device 100 is not limited to the above components, but may include alternative or additional components, as would be understood by one of ordinary skill in the art.

For example, it will be understood by one of ordinary skill in the art that infusion device 100 may include any number of bubble sensors (e.g., one or more) or a split bubble sensor positioned at substantially the same or different points along pathway 110 in order to sense bubbles in tubing 112. The number of bubble sensors may be selected based on desired safety and cross-check concerns for detecting bubbles in the fluid being infused.

For another example, infusion device 100 may include a third module 190. Third module 190 is a total volume counter module. Third module 190 is in communication with bubble sensors 150, and is configured to record a total combined volume of bubbles detected by bubble sensors 150 during one or several infusion events. Third module 190 may be programmed to subtract from this value the volume of any air removed from tubing 112 by a user of infusion device 100. For example, if first module 170 or second module 180 generates an alarm, a user of infusion device 100 may remove one or more air bubbles from tubing 112. Third module 190 may be configured to subtract the volume of any bubbles removed from tubing 112 by the user from the total combined volume of bubbles recorded by third module 190. Third module 190 may be programmed to display the total combined volume on a display device of infusion device 100.

Third module 190 may further be configured to generate a third alarm condition when the total combined volume of bubbles exceeds a third preselected threshold. In an exemplary embodiment, a user of infusion device 100 may preselect a threshold volume for the third module 190. Third module 190 may then record the total combined volume of bubbles detected by bubble sensors 150 over the entire course of an infusion event. When the total combined volume exceeds the third threshold, third module 190 generates a "total air volume" alarm condition. As with the first and second modules, the third module may be programmed to display the total air volume alarm and/or deactivate pump 130 when the alarm is triggered.

Alternatively, third module 190 may not generate any alarm. To the contrary, third module 190 may be configured to merely displayed the recorded total air volume on a display device of infusion device 100. The third module may be programmed to be cleared only when a new infusion is started.

Figure 2:
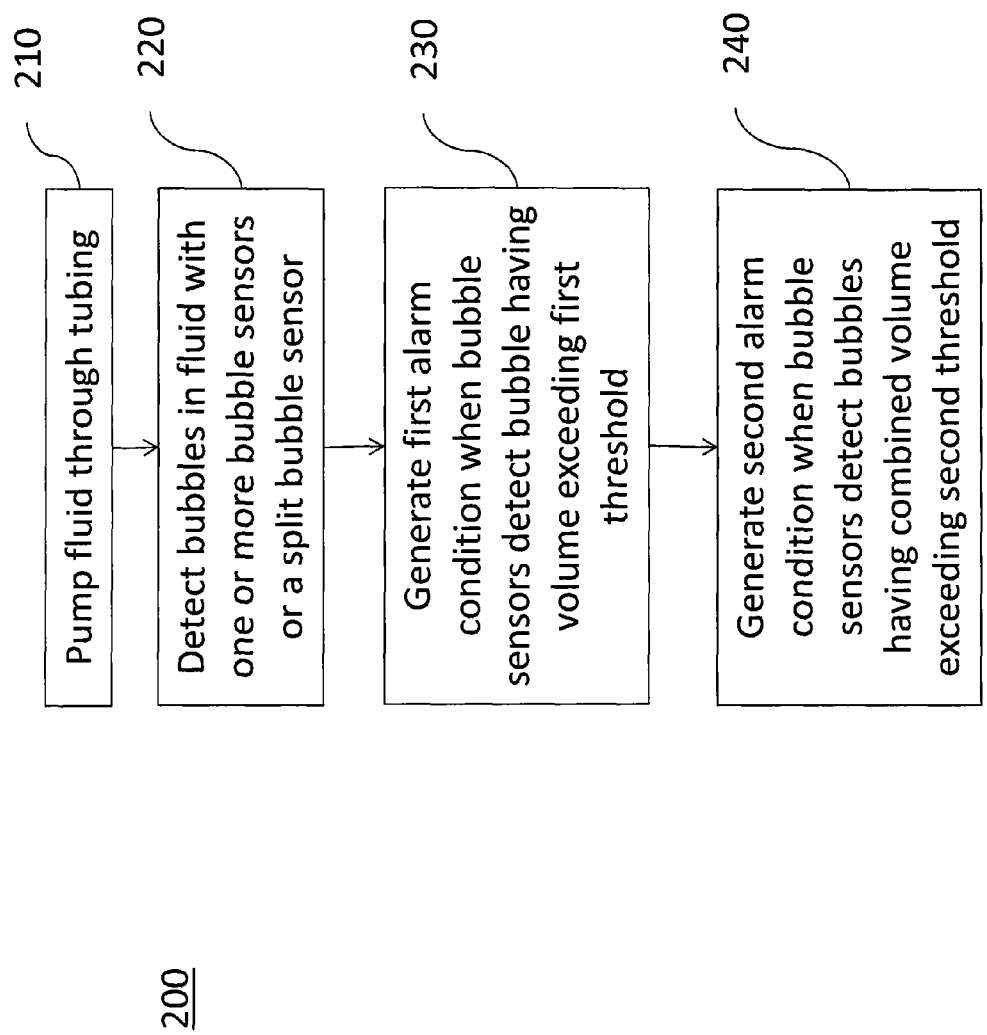
FIG. 2 is a diagram illustrating an exemplary method for sensing bubbles during fluid infusion in accordance with aspects of the present invention.

FIG. 2 shows an exemplary method 200 for sensing bubbles during fluid infusion in accordance with aspects of the present invention. As a general overview, method 200 includes pumping fluid through tubing, detecting bubbles with one or more bubble sensors, generating a first alarm condition, and generating a second alarm condition. Additional details of method 200 are described herein with respect to the components of infusion device 100.

In step 210, fluid is pumped through tubing. In an exemplary embodiment, infusion device 100 is programmed with at least one infusion protocol. When tubing 112 is received within pathway 110, processor 190 controls pump 130 to pump fluid through tubing 112 in accordance with the at least one infusion protocol.

In step 220, one or more bubbles are detected in the fluid. In an exemplary embodiment, bubble sensors 150 detect bubbles in the fluid being pumped through tubing 112. The detection of bubbles using bubble sensors 150 will be understood by one of ordinary skill in the art from the description herein.

In step 230, a first alarm condition is generated. In an exemplary embodiment, first module 170 generates an alarm condition when bubble sensors 150 detect a bubble having a volume above, but not limited to, a first preselected threshold. As explained above, the threshold may be within the range of 0.02-0.30 ml. First module 170 may also be programmed to deactivate pump 130 until the detected bubble is cleared from tubing 112.

In step 240, a second alarm condition is generated. In an exemplary embodiment, second module 180 generates an alarm condition when bubble sensors 150 detect a plurality of bubbles over a preselected period of time having a combined volume above a second preselected threshold. As explained above, the period of time may be within the range of 1-15 minutes, and the volume threshold may be within the range of 0.5-3.8 ml. Second module 180 may also be programmed to deactivate pump 130 until at least a portion of the detected bubbles are cleared from tubing 112.

It will be understood that method 200 is not limited to the above steps, but may include alternative steps and additional steps, as would be understood by one of ordinary skill in the art from the description herein.

For one example, it may be desirable to record the total combined volume of bubbles detected during an infusion event. Accordingly, method 200 may include the step of recording a total combined volume of bubbles detected by bubble sensors 150 during an infusion event with third module 190. As explained above, the volume of any bubbles removed from tubing 112 by a user may be subtracted from the total combined volume record by third module 190. Additionally, third module 190 may be programmed to display the total combined volume on a display device of infusion device 100. Third module 190 may further be programmed to generate a third alarm condition when the total combined volume of bubbles exceeds a third preselected threshold. Additional modules may also be added to perform various calculations, as would be understood by one of ordinary skill in the art.

Although the invention is illustrated and described herein with reference to specific embodiments, the invention is not intended to be limited to the details shown. Rather, various modifications may be made in the details within the scope and range of equivalents of the claims and without departing from the invention.

What is claimed:

1. An infusion device comprising:
a pathway which receives tubing therein;
at least one pump adjacent the pathway having the tubing therein, the at least one pump altering the pathway to pump fluid through the tubing; and
one or more bubble sensors positioned adjacent the pathway, the one or more bubble sensors configured to detect bubbles in the fluid being pumped through the tubing;
a first module in communication with the one or more bubble sensors, the first module configured to generate a first alarm condition when the one or more bubble sensors detect a bubble having a first volume above a first preselected threshold, the first alarm providing an indication to a user to remove the bubble having the first volume from the tubing;
a second module in communication with the one or more bubble sensors, the second module configured to generate a second alarm condition when the one or more bubble sensors detect a plurality of bubbles over a preselected period of time collectively having a second volume above a second preselected threshold, the second alarm providing an indication to the user to remove the plurality of bubbles collectively having the second volume from the tubing; and
a third module in communication with the one or more bubble sensors, the third module configured to record a total combined volume of bubbles detected by the one or more bubble sensors during an infusion event, the third module programmed to (i) subtract the first volume from the total combined volume when the first module indicates the user is to remove the bubble having the first volume from the tubing and (ii) subtract the second volume from the total combined volume when the second module indicates the user is to remove the plurality of bubbles collectively having the second volume from the tubing.

2. The infusion device of claim 1, wherein the first module is programmed to deactivate the pump when the first alarm condition is generated.

3. The infusion device of claim 1, wherein the first preselected threshold is within the range of 0.02-0.30 ml.

4. The infusion device of claim 1, wherein the second module is programmed to deactivate the pump when the second alarm condition is generated.

5. The infusion device of claim 1, wherein the preselected period of time is within the range of 1-15 minutes, and the second preselected threshold is within the range of 0.5-3.8 ml.

6. The infusion device of claim 1, wherein the third module is configured to generate a third alarm condition when the total combined volume of bubbles exceeds a third preselected threshold.

7. The infusion device of claim 1, wherein the third module is configured to display the total combined volume of bubbles the a user on a display device of the infusion device.

8. A method for sensing bubbles during fluid infusion comprising the step of:
- pumping fluid through tubing using at least one pump positioned adjacent a pathway having the tubing therein to alter the pathway having the tubing therein;
- detecting bubbles in the fluid being pumped through the tubing with one or more bubble sensors;
- generating a first alarm condition when the one or more bubble sensors detect a bubble having a first volume above a first preselected threshold;
- generating a second alarm condition when the one or more bubble sensors detect a plurality of bubbles over a preselected period of time collectively having a second volume above a second preselected threshold;
- recording a total combined volume of bubbles detected by the one or more bubble sensors during an infusion event; and
- enabling removal of the bubble having the first volume from the tubing responsive to the generation of the first alarm;
- subtracting the first volume from the total combined volume responsive to the removal of the bubble having the first volume from the tubing;
- enabling removal of the plurality of bubbles having the second volume from the tubing responsive to the generation of the second alarm; and
- subtracting the second volume from the total combined volume responsive to the removal of the plurality of bubbles collectively having the second volume from the tubing.

9. The method of claim 8, further comprising the step of deactivating the pump when one of the first and second alarm conditions is generated.

10. The method of claim 8, wherein the first preselected threshold is within the range of 0.02-0.30 ml.

11. The method of claim 8, wherein the preselected period of time is within the range of 1-15 minutes, and the second preselected threshold is within the range of 0.5-3.8 ml.

12. The method of claim 8, further comprising the step of generating a third alarm condition when the total combined volume of bubbles exceeds a third preselected threshold.

13. The method of claim 8, further comprising the step of displaying the total combined volume of bubbles to the user on a display device of an infusion device.

* * * * *